US008034761B2

(12) United States Patent
Widder et al.

(10) Patent No.: US 8,034,761 B2
(45) Date of Patent: Oct. 11, 2011

(54) USE OF A MIXTURE OF CIS- AND TRANS-3-METHYL-γ-DECALACTONE AND COMPOSITIONS OF ODORIFEROUS SUBSTANCES AND PERFUMED ARTICLES COMPRISING SAID MIXTURE

(75) Inventors: Sabine Widder, Holzminden (DE); Christopher Sabater, Holzminden (DE); Jan Looft, Holzminden (DE); Tobias Vössing, Beverungen (DE); Marcus Eggers, Beverungen (DE); Thomas Obrocki, Pattensen (DE); Johannes Panten, Lüchtringen (DE)

(73) Assignee: Symrise AG, Holzminden (DE)

( * ) Notice: Subject to any disclaimer, the term of this patent is extended or adjusted under 35 U.S.C. 154(b) by 423 days.

(21) Appl. No.: 11/570,847

(22) PCT Filed: Jun. 6, 2005

(86) PCT No.: PCT/EP2005/052581

§ 371 (c)(1), (2), (4) Date: Dec. 5, 2007

(87) PCT Pub. No.: WO2005/123889

PCT Pub. Date: Dec. 29, 2005

(65) Prior Publication Data

US 2008/0194455 A1 Aug. 14, 2008

(30) Foreign Application Priority Data

Jun. 19, 2004 (DE) ......................... 10 2004 029 809

(51) Int. Cl.
*A61K 8/00* (2006.01)

(52) U.S. Cl. ........................................................ 512/11

(58) Field of Classification Search ..................... 512/11
See application file for complete search history.

(56) References Cited

FOREIGN PATENT DOCUMENTS

| | | |
|---|---|---|
| EP | 0513627 | 11/1992 |
| JP | 200086647 | 3/2000 |

OTHER PUBLICATIONS

J. Cossy et al., Synlett 2001, No. 5, pp. 629-633. No month available.*

Wu Yikang et al: "Synthesis of natural fragrant molecules cis-3-methyl-4-decanolide and aerangis lactone. General enantioselective routes to beta, gamma-cis-disubstituted gamma-lactones and gamma, delta-cis-disubstituted delta-lactones" Journal of Organic Chemistry, Bd. 67, Nr. 11, May 31, 2002, XP0023487.

Masuzawa y et al., Synthesis of both enantimoers of cis-3-methyl-4-decanolide, a key component for the scent of African orhids, Database Embase 'Online! Elsevier Science Publishers, Amsterdam, NL; 1999, XP002342878.

Database WPI Section CH, Week 200026 Derwent Publications Ltd., London, GB, AN 2000-298537, XP002342880.

* cited by examiner

*Primary Examiner* — John Hardee
(74) *Attorney, Agent, or Firm* — Roylance, Abrams, Berdo & Goodman, L.L.P.

(57) ABSTRACT

The use of a mixture which comprises cis- and trans-3-methyl-γ-decalactone in a molar ratio in the range of 2:3 to 3:2, as a jasmone fragrance is described.

20 Claims, No Drawings

1

USE OF A MIXTURE OF CIS- AND TRANS-3-METHYL-γ-DECALACTONE AND COMPOSITIONS OF ODORIFEROUS SUBSTANCES AND PERFUMED ARTICLES COMPRISING SAID MIXTURE

FIELD OF THE INVENTION

The present invention relates to the use of a mixture of cis- and trans-3-methyl-γ-decalactone, fragrance compositions containing such a mixture and perfumed articles, and a process for the production of a fragrance composition.

BACKGROUND OF THE INVENTION

Despite a plurality of already existing fragrances, there is also furthermore in the perfume industry a general demand for new fragrances which have in addition to their primary, namely odour properties additional positive secondary properties, such as e.g. a higher stability under certain application conditions, a higher yield or a better adhesion capacity, or even, due to synergy effects with other fragrances, lead to better sensory profiles.

Thus for example by using substances with a more substantial character and better sensory profile, the quantities used and the number of fragrances in formulations can be minimised, which leads to a sustainable conservation of resources in the perfuming of consumer and consumption goods.

There is therefore in the perfume industry a demand for further fragrances with better and more substantial sensory profiles.

In particular, there is in the perfume industry a demand for fragrances with a jasmone odour (jasmone fragrances). By this is to be understood in the context of the present text an odour that is similar to the odour of naturally occurring cis-jasmone. The odour of cis-jasmone is described in the literature as follows: fruity, celery-like scent, in dilution sweet-flowery, reminiscent of jasmine and cherry blossom.

SUMMARY OF THE INVENTION

It was therefore the primary object of the present invention to give a novel jasmone fragrance.

According to the invention, this primary object is achieved by the use of a mixture that comprises cis- and trans-3-methyl-γ-decalactone in a molar ratio in the range of 2:3.5 to 3.5:2, as a jasmone fragrance.

The term cis- or trans-3-methyl-γ-decalactone thereby comprises the pure (cis or trans) enantiomers and enantiomer mixtures thereof, in particular the racemic mixtures.

The invention is based on the surprising knowledge that a mixture of cis- and trans-3-methyl-γ-decalactone is suitable as a jasmone fragrance, although the individual substances are not jasmone fragrances.

The structural formula of a mixture of cis- and trans-3-methyl-γ-decalactone is shown below:

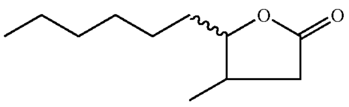

Mixtures of cis- and trans-3-methyl-γ-decalactone and the individual compounds are known from the literature:

*Chem. Express* 1992, 7, 901 describes the photochemical synthesis of the racemic mixture of cis- and trans-3-methyl-γ-decalactone.

2

In *Synlett* 2001, 5, 629 is described the synthesis of cis, trans-3-methyl-γ-decalactone on a solid phase system based on a crotyl stannane reagent and heptanal.

*J. Am. Chem. Soc.* 1979, 101, 4752 describes an electrochemical variant for the preparation of racemic cis/trans-3-methyl-7-decalactone. No description of the odour is given.

*Helv. Chim. Acta* 2001, 84, 3428 and also *J. Org. Chem.* 2002, 67, 3802 describe enantioselective syntheses of cis-3-methyl-γ-decalactone.

In his book "Vom Duft der Orchideen", Ed.: Editiones Roche, F. Hoffmann-LaRoche A G, Basel, 1993, R. Kaiser describes for the first time the existence of cis-3-methyl-γ-decalactone in nature (*Aeringis kirkii*).

In Izvestiya Akademii Nauk SSSR, Seriya Khimicheskaya, 1971, 2, 389 is given a general specification for the preparation of cis/trans-lactones. The substance cis/trans-3-methyl-γ-decalactone itself is not mentioned explicitly, but it can be prepared from the general specification.

In *J. Essent. Oil Res.* 1996, 8, 587 it is described that the substance 3-methyl-4-decanolide occurs in blood oranges and a description of the odour is given lactonic, peach, coconut.

The substance is mentioned in the *Proceedings of the 9$^{th}$ Congress of Ess. Oils* (*Singapore*) 1984, *Book* 3, 69, as a novel constituent of clary sage oil with a trans structure and typically lactonic note.

*Nat. Product Lett.* 1999, 13, 239 describes the enantioselective synthesis of the cis compounds (3R,4R)-3-methyl-4-decanolide and (3S,4S)-3-methyl-4-decanolide. Spectroscopic data are given, but no descriptions of scent.

In JP-A2 2000-086647 is described an enantioselective synthesis for both enantiomers of the cis-3-methyl-γ-decalactone. The use in perfume oils and flavourings is described.

JP-A2 09-169624 relates to the application of $C_{11}$-$C_{16}$-γ-lactones as antimicrobial active ingredients in toothpaste and mouthwash.

The fact that a mixture of two isomers compared with the pure isomers is preferably suitable as a fragrance, is surprising.

Thus the main attention of the synthesising fragrance chemist and compounding perfumer is generally directed to the fact that with compounds with different stereoisomers, the one preferably to be isolated, analysed, produced and used is the one that has the greatest impact or is most typical of the odour of a structure. In the actual investigations, there resulted for cis-3-methyl-γ-decalactone an odour threshold value of 24.6 μg/l (from water) and for trans-3-methyl-γ-decalactone a threshold value of 216 μg/l (from water). Accordingly, the perfumers also classified the strength of the two pure isomers on a scale of 1-6 (see below). The perfumers were in addition given different mixtures for evaluation:

| Mixture (cis:trans) | Strength | Odour |
|---|---|---|
| 100:0 | 4 | strong, coconut, lactonic, not peach |
| 80:20 | 5 | coconut, soft, creamy, milky, driest |
| 60:40 | 6 | strongly jasmone, strongest, fruity, coconut, peach |
| 40:60 | 5 | jasmone, fruity, fresh top note, lively, flowery, strongly peach |
| 20:80 | 3 | fruity, peach, compact, weaker, sweetish |
| 0:100 | 1 | weakest, peach |

Surprisingly, however, the perfumers did not rate either the pure cis isomer with its coconut aspects or the pure trans isomer with its fruity peach aspects as the sensorily most valuable product, but according to the above table the mixtures of the two isomers with a molar cis/trans ratio of 60:40 or 40:60 (thus 3:2 or 2:3). This applies both with regard to the olfactory rating and to the application criteria such as adhesion to smelling strips and radiation.

The optimum mixture ratio of the isomers is approximately a cis concentration of 36.4-63.6% and a corresponding trans concentration of 63.6-36.4%.

A further aspect of the present invention relates to the use of cis-3-methyl-γ-decalactone in a trans-3-methyl-γ-decalactone-containing fragrance composition to enhance the peach odour produced by trans-3-methyl-γ-decalactone. Interestingly, the peach odour of the trans-3-methyl-γ-decalactone can be enhanced by addition of cis-3-methyl-γ-decalactone, although the cis compound itself does not have such a peach odour; the cis compound acts as an enhancer. From what has been said, it results that a jasmone odour aspect is added at the same time which cannot be detected either in the pure cis or in the pure trans compound.

The invention also relates to a process for producing, enhancing or modifying a jasmone odour in a fragrance composition, wherein a quantity of a mixture of cis- and trans-3-methyl-γ-decalactone in a molar ratio in the range of 2:3.5 to 3.5:2 which is sufficient to produce, enhance or modify a jasmone odour is added to the fragrance composition. If therefore for example a fragrance composition which initially does not have a jasmone odour is used as the basis, this fragrance composition can be provided with a jasmone odour by adding the said mixture of cis- and trans-3-methyl-γ-decalactone. Of course, a quantity of the mixture which is sufficient to produce the jasmone odour within the fragrance composition produced must thereby be used. On the basis of a fragrance composition which already has a jasmone odour, an enhancement or modification of the jasmone odour can be created by addition of the mixture of cis- and trans-3-methyl-γ-decalactone.

The invention further relates to a process for the preparation of a fragrance composition with a strong peach odour and a jasmone odour, with the following steps:

- preparation of a basic fragrance composition which does not have a strong peach odour
- mixing the basic fragrance composition with the compounds cis-3-methyl-γ-decalactone and trans-3-methyl-γ-decalactone, with the proviso that (i) these compounds are used in a molar cis/trans ratio in the range of 2:3.5 to 3.5:2, (ii) the total quantity of the compounds used is sufficient to produce the strong peach odour and the jasmone odour and (iii) the quantity of trans-3-methyl-γ-decalactone used is not sufficient, in the absence of cis-3-methyl-γ-decalactone, to produce the strong peach odour.

With this process according to the invention, on the basis of a basic fragrance composition which does not have a strong peach odour, a fragrance composition with a strong peach odour is prepared by adding a compound (trans-3-methyl-γ-decalactone) which is itself only able to produce a weak peach odour and additionally a compound (cis-3-methyl-γ-decalactone) which is suitable for enhancing the peach odour produced by trans-3-methyl-γ-decalactone, is added as an enhancer.

The invention also relates to a process for enhancing a peach odour produced by trans-3-methyl-γ-decalactone in a fragrance composition, wherein an effective quantity of cis-3-methyl-γ-decalactone is added to the fragrance composition.

Also subject matter of the present invention is a fragrance composition or a perfumed article with a jasmone odour, comprising a quantity, creating the jasmone odour, of a mixture of cis- and trans-3-methyl-γ-decalactone in a molar cis/trans ratio in the range of 2:3.5 to 3.5:2, wherein neither the cis-3-methyl-γ-decalactone used on its own nor the trans-3-methyl-γ-decalactone used on its own creates the jasmone odour.

Such a fragrance composition or such a perfumed article thereby has a strong peach odour.

If the fragrance composition with jasmone odour is a perfume oil composition, the quantity of the mixture of cis- and trans-3-methyl-γ-decalactone used is preferably in the range of 0.01 to 99.9 wt. %, preferably 0.1 to 90 wt. % and particularly preferably 0.5 to 70 wt. %, based on the total weight of the perfume oil composition.

The olfactory properties, material properties (such as solubility in common cosmetic solvents, compatibility with the common other constituents of products of that type, etc.), and the toxicological harmlessness of the mixture to be used according to the invention underline the particular suitability thereof for the named purposes.

Particularly preferred are fragrance compositions or perfumed articles according to the invention which contain a quantity of a mixture of cis- and trans-3-methyl-γ-decalactone which is not only sufficient to produce a jasmone odour but also to produce, modify and/or enhance a peach-like or coconut-like odour note.

DETAILED DESCRIPTION OF THE INVENTION

In the preparation of fragrance compositions according to the invention, jasmone or peach-, coconut- and lactone-like odour notes can be used in diverse variations. The example below of a perfume scent ("Jenny") demonstrates in a clear way the olfactory effect of a mixture of cis/trans-3-methyl-γ-decalactone. A perfume oil of the "Jenny" type can be characterised as flowery, modern and transparent. The base perfume oil already contains the trans-3-methyl-γ-decalactone; by the addition of cis-3-methyl-γ-decalactone, the fruity (peach-like) notes become surprisingly clearly enhanced and the fragrance composition also acquires a jasmone aspect.

A mixture of cis-/trans-3-methyl-γ-decalactone (with a molar ratio in the range of 2:3.5 to 3.5:2) is, despite its olfactory properties, suitable especially for use in perfume compositions. The cis/trans mixture can be combined with a plurality of other fragrances and used in numerous products. The compound can be combined particularly advantageously with other fragrances in different quantity ratios to novel perfume compositions.

A fragrance composition with a peach, coconut and lactone note can be prepared for example by mixing the mixture of cis- and trans-3-methyl-γ-decalactone with constituents of a basic fragrance composition, wherein the mixture of cis- and trans-3-methyl-γ-decalactone is used in a quantity which is sufficient to modify and/or enhance the odour of the basic fragrance composition.

Examples of fragrances with which the mixture to be used according to the invention can be advantageously combined are found e.g. in S. Arctander, Perfume and Flavor Chemicals, Vols. I and II, Montclair, N.J., 1969, self-published, or K. Bauer, D. Garbe and H. Surburg, Common Fragrance and Flavor Materials, 4$^{rd}$. Ed., Wiley-VCH, Weinheim 2001.

Individually can be named:

Extracts from natural raw materials such as essential oils, concretes, absolutes, resins, resinoids, balsams and tinctures such as e.g.

ambergris tincture; amyris oil; angelica seed oil; angelica root oil; aniseed oil; valerian oil; basil oil; wood moss absolute;

bay oil; mugwort oil; benzoin resin; bergamot oil; beeswax absolute; birch tar oil; bitter almond oil; savoury oil; bucco leaf oil; cabreuva oil; cade oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill herb oil; dill seed oil; eau de brouts absolute; oakmoss absolute; elemi oil; tarragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calmus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil; spike lavender oil; Japanese anise oil; styrax oil; tagetes oil; fir needle oil; tea-tree oil; terpentine oil; thyme oil; Tolu balsam; tonka absolute; tuberose absolute; vanilla extract; violet leaf absolute; verbena oil; vetiver oil; juniper berry oil; wine lees oil; wormwood oil; wintergreen oil; ylang oil; hyssop oil; civet absolute; cinnamon leaf oil; cinnamon bark oil and fractions thereof, or ingredients isolated therefrom;

individual fragrances from the group of hydrocarbons, such as e.g. 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

of aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

of aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethylacetal; 1,1-dimethoxy-2,2,5-trimethyl-4-hexene; citronellyl oxyacetaldehyde; 1-(1-methoxypropoxy)-(E/Z)-3-hexene;

of aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

of aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of aliphatic nitriles such as e.g. 2-nonenitrile; 2-undecenenitrile; 2-tridecenenitrile; 3,12-tridecadienenitrile; 3,7-dimethyl-2,6-octadienenitrile; 3,7-dimethyl-6-octenenitrile;

of esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octynoate; methyl-2-nonynoate; allyl-2-isoamyloxyacetate; methyl-3,7-dimethyl-2,6-octadienoate; 4-methyl-2-pentylcrotonate;

of acyclic terpene alcohols such as e.g. citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

of acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal thereof;

of cyclic terpene alcohols such as e.g. menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates thereof;

of cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-iron; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methyl cedryl ketone);

of cyclic alcohols such as e.g. 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols such as e.g. alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,6-trimethylcyclohexyl)hexan-3-ol;

of cyclic und cycloaliphatic ethers such as e.g. cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic and macrocyclic ketones such as e.g. 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

of cycloaliphatic aldehydes such as e.g. 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexencarbaldehyde; 4-(4-methyl-3-penten-1-yl)-3-cyclohexencarbaldehyde;

of cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl)ketone;

of esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexylacetate; decahydro-2-naphthylacetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, or 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

of esters of cycloaliphatic alcohols such as e.g. 1-cyclohexylethyl crotonate;

of esters of cycloaliphatic carboxylic acids such as e.g. allyl-3-cyclohexyl propionate; allyl cyclohexyloxyacetate; cis- and trans-methyldihydrojasmonate; cis- and trans-methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolan-2-acetate;

of araliphatic alcohols such as e.g. benzyl alcohol; 1-phenylethyl alcohol; 2-phenylethyl alcohol; 3-phenyl propanol; 2-phenyl propanol; 2-phenoxyethanol; 2,2-dimethyl-3-phenyl propanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichlormethylbenzyl acetate; alpha,alpha-dimethylphenylethyl acetate; alpha, alpha-dimethylphenylethyl butyrate; cinnamyl acetate; 2-phenoxyethyl isobutyrate; 4-methoxybenzyl acetate;

of araliphatic ethers such as e.g. 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

of aromatic and araliphatic aldehydes such as e.g. benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 2-methyl-3-(4-isobutylphenyl) propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylendioxybenzaldehyde; 3,4-dimethoxybenzaldehyde; 2-methyl-3-(4-methoxyphenyl)propanal; 2-methyl-3-(4-methylendioxyphenyl)propanal;

of aromatic and araliphatic ketones such as e.g. acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenylglycidate; ethyl-3-methyl-3-phenylglycidate;

of nitrogen-containing aromatic compounds such as e.g. 2,4,6-trinitro-1,3-dimethyl-5-tert.-butylbenzene; 3,5-dinitro-2,6-dimethyl-4-tert.-butylacetophenone; cinnamonitrile; 3-methyl-5-phenyl-2-pentenenitrile; 3-methyl-5-phenylpentanenitrile; methyl anthranilate; methyl-N-methylanthranilate; Schiff bases of methyl anthranilate with 7-hydroxy-3,7-dimethyloctanal, 2-methyl-3-(4-tert.-butylphenyl) propanal or 2,4-dimethyl-3-cyclohexenecarbaldehyde; 6-isopropylquinoline; 6-isobutylquinoline; 6-sec.-butylquinoline; 2-(3-phenylpropyl)pyridine; indole; skatole; 2-methoxy-3-isopropylpyrazine; 2-isobutyl-3-methoxypyrazine;

of phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

of heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecandioate; ethylene-1,13-tridecandioate; coumarin; 2,3-dihydrocoumarin; octahydrocoumarin.

The perfume oils containing the lactone mixture to be used according to the invention can be used in liquid form, undiluted or diluted with a solvent for perfumings. Suitable solvents for this are e.g. ethanol, isopropanol, diethylene-glycol monoethyl ether, glycerol, propylene glycol, 1,2-butylene glycol, dipropylene glycol, diethyl phthalate, triethyl citrate, isopropyl myristate etc.

Furthermore, the perfume oils containing the lactone mixture to be used according to the invention can be adsorbed on a carrier which provides both for a fine distribution of the fragrances in the product and also for a controlled release during application. Carriers of this type can be porous inorganic materials such as light sulfate, silica gels, zeolites, gypsums, clays, clay granules, gas concrete etc. or organic materials such as woods and cellulose-based substances.

The perfume oils containing the lactone mixture to be used according to the invention can also be present microencapsulated, spray-dried, as inclusion complexes or as extrusion products and be added in this form to the product to be perfumed.

Optionally the properties of the perfume oils modified in this way can be further optimised by so-called "coating" with suitable materials with regard to a more targeted scent release, for which purpose preferably wax-like plastics such as e.g. polyvinyl alcohol are used.

The microencapsulation of the perfume oils can be carried out for example by the so-called coacervation process using capsule materials e.g. composed of polyurethane-like materials or soft gelatine. The spray-dried perfume oils can be prepared for example by spray-drying an emulsion containing the perfume oil, or dispersion wherein modified starches, proteins, dextrin and vegetable gums can be used as carriers. Inclusion complexes can be prepared e.g. by introducing dispersions of the perfume oil and cyclodextrins or urea derivatives into a suitable solvent, e.g. water. Extrusion products can be obtained by melting the perfume oils with a suitable wax-like substance and by extrusion with subsequent solidification, optionally in a suitable solvent, e.g. isopropanol.

The perfume oils containing the lactone mixture to be used according to the invention can be used in concentrated form, in solutions or in the modified form described above, for the preparation of e.g. perfume extracts, eaux de parfum, eaux de toilette, aftershave lotions, eaux de Cologne, pre-shave products, splash colognes and perfumed freshening wipes and the perfuming of acid, alkaline and neutral cleaning agents such as e.g. floor cleaners, window cleaners, dishwashing detergents, bath and sanitary cleaners, scouring milk, solid and liquid toilet cleaners, powder and foam carpet cleaners, liquid detergents, powder detergents, laundry pre-treatment agents such as bleaching agents, soaking agents and stain removers, fabric softeners, washing soaps, washing tablets, disinfectants, surface disinfectants and air fresheners in liquid or gel form or applied to a solid carrier, aerosol sprays, waxes and polishes such as furniture polishes, floor waxes, shoe creams and personal hygiene products such as e.g. solid and liquid soaps, shower gels, shampoos, shaving soaps, shaving foams, bath oils, cosmetic emulsions of the oil-in-water, water-in-oil and water-in-oil-in-water type such as e.g. skin creams and lotions, face creams and lotions, sun protection creams and lotions, after-sun creams and lotions, hand creams and lotions, foot creams and lotions, depilatory creams and lotions, aftershave creams and lotions, tanning creams and lotions, haircare products such as e.g. hairsprays, hair gels, solid hair lotions, hair rinses, permanent and semi-permanent hair colorants, hair styling products such as cold waves and hair smoothing products, hair lotions, hair creams and lotions, deodorants and antiperspirants such as e.g. underarm sprays, roll-ons, deodorant sticks, deodorant creams, products for decorative cosmetics such as e.g. eye shadows, nail varnishes, foundations, lipsticks, mascara and candles, lamp oils, joss sticks, insecticides, repellents and propellants.

In fragrance compositions, the total quantity used of the lactone mixture to be used according to the invention is 0.01 to 99.9 wt. %, preferably 0.1 to 90% and particularly preferably 0.5 to 70%, based on the total fragrance composition.

Examples

1. Perfume Compositions

Reference example for a perfume oil of the "Jenny" type addition of cis-3-methyl-γ-decalactone to a basic formulation:

| | Basic perfume oil | Modified perfume oil |
|---|---|---|
| Benzyl acetate | 5.00 | 5.00 |
| Bergamote oil colorless | 20.00 | 20.00 |
| 7-Methyl-2H-1,5-benzodioxepin-3(4H)-one 10% DPG | 5.00 | 5.00 |
| Citronellol inactive | 10.00 | 10.00 |
| 2,4,4,7-Tetramethyl-oct-6-en-3-one | 5.00 | 5.00 |
| Dimethylbenzylcarbinylacetate | 10.00 | 10.00 |
| Ethyl acetoacetate | 5.00 | 5.00 |
| Ethyl linalool | 60.00 | 60.00 |
| Cyclohexadec-8-enone 100P. | 255.00 | 255.00 |
| Methyl dihydrojasmonate | 280.00 | 280.00 |
| Helional | 5.00 | 5.00 |
| Hexenol cis-3 10% DPG | 10.00 | 10.00 |
| Hexyl cinnamic aldehyde | 40.00 | 40.00 |
| Ionone beta | 15.00 | 15.00 |
| Isodamascone 1% DPG | 10.00 | 10.00 |
| 2-Methyl-4-phenyl-[1,3]dioxolane 10% DPG | 5.00 | 5.00 |
| Lemon oil clear | 15.00 | 15.00 |
| 4-tert.-Butyl-α-methyldihydrocinnamaldehyde | 20.00 | 20.00 |
| Linalool synth. | 30.00 | 30.00 |
| 2,2-Dimethyl-3-(3-methylphenyl)propanol | 10.00 | 10.00 |
| Mandarine oil clear | 10.00 | 10.00 |
| Nerolidol | 20.00 | 20.00 |
| Patchouli oil indo. 10% DPG | 10.00 | 10.00 |
| 3-Methyl-5-phenylpentanol | 40.00 | 40.00 |
| Phenylethyl alcohol | 10.00 | 10.00 |
| Rosewood oil bras. | 10.00 | 10.00 |
| Sandalwood oil East India | 5.00 | 5.00 |
| 3-(5,5,6-Trimethyl-bicyclo[2.2.1]hept-2-yl)-cyclohexanol | 20.00 | 20.00 |
| Tagette oil 10% DPG | 10.00 | 10.00 |
| 2,4,6-Trimethyl-4-phenyl-1,3-dioxane coeur 10% DPG | 5.00 | 5.00 |
| Ylang ylang oil extra 10% DPG | 5.00 | 5.00 |
| Trans-3-methyl-γ-decalactone | 20.00 | 20.00 |
| DPG (dipropylene glycol) | 20.00 | — |
| Cis-3-methyl-γ-decalactone | — | 20.00 |
| | 1000.00 | 1000.00 |

The basic perfume oil of the "Jenny" type becomes more flowery, hedione-like and jasmone-like by the addition of cis-3-methyl-γ-decalactone (instead of the sensorily ineffective solvent DPG); the fruity (peach-like) aspects are enhanced.

2. Preparation

The preparation of cis- and trans-3-methyl-γ-decalactone is carried out in a known way according to the process description from the following literature reference: Izvestiya Akademii Nauk SSSR, Seriya Khimicheskaya, 1971, 2, 389.

The invention claimed is:

1. A process for preparing a jasmone fragrance, that comprises adding cis-methyl-γ-decalactone to a mixture comprising trans-3-methyl-γ-decalactone, wherein a quantity of cis- and trans-methyl-γ-decalactone is in a molar ratio in the range of 2:3.5 to 3.5:2.

2. A process for adding or enhancing a peach odour in a preparation by adding cis-3-methyl-γ-decalactone to a fragrance composition containing trans-3-methyl-γ-decalactone to enhance the peach odour produced by trans-3-methyl-γ-decalactone.

3. A process for producing, enhancing or modifying a jasmone odour in a fragrance composition comprising adding cis-methyl-γ-decalactone to said fragrance composition comprising trans-3-methyl-γ-decalactone, wherein a quantity of cis- and trans-methyl-γ-decalactone is in a molar ratio in a range of 2:3.5 to 3.5:2 which is sufficient to produce, enhance or modify a jasmone odour, is added to the fragrance composition.

4. A process for the preparation of a fragrance composition with a strong peach odour and a jasmone odour, with the following steps:

preparing a basic fragrance composition which does not have a strong peach odour mixing said basic fragrance composition with trans-3-methyl-γ-decalactone, adding cis-methyl-γ-decalactone to said basic fragrance composition comprising trans-3-methyl-γ-decalactone, wherein (i) these compounds are used in a molar cis/trans ratio in the range of 2:3.5 to 3.5:2, (ii) the total quantity of the compounds used is sufficient to produce a strong peach odour and a jasmone odour and (iii) the quantity of trans-3-methyl-γ-decalactone used is not sufficient in the absence of cis-3-methyl-γ-decalactone to produce the strong peach odour.

5. A process for enhancing a peach odour produced by trans-3-methyl-γ-decalactone in a fragrance composition, by adding an effective quantity of cis-3-methyl-γ-decalactone to said fragrance composition.

6. A perfume composition with a jasmone odour comprising a mixture of cis-3-methyl-γ-decalactone and trans-3-methyl-γ-decalactone in a molar cis/trans ratio in a range of 2:3.5 to 3.5:2, wherein neither the cis-3-methyl-γ-decalactone used on its own nor the trans-3-methyl-γ-decalactone used on its own produces said jasmone odour, and a fragrance selected from the group consisting of extracts from natural raw materials such as essential oils, concretes, absolutes, resins, resinoids, balsams and tinctures; and individual fragrances from the group of hydrocarbons;

aliphatic alcohols;
aliphatic aldehydes and acetals thereof;
aliphatic ketones and oximes thereof;
aliphatic sulfur-containing compounds;
aliphatic nitriles;
acyclic terpene alcohols;
acyclic terpene aldehydes and ketones;
cyclic terpene alcohols;
cyclic terpene aldehydes and ketones;
cyclic alcohols;
cycloaliphatic alcohols;
cyclic and cycloaliphatic ethers;
cyclic and macrocyclic ketones;
cycloaliphatic aldehydes;
cycloaliphatic ketones;
esters of cyclic alcohols;
esters of cycloaliphatic alcohols;
esters of cycloaliphatic carboxylic acids;
araliphatic alcohols;
esters of araliphatic alcohols and aliphatic carboxylic acids;
araliphatic ethers;
aromatic and araliphatic aldehydes;
aromatic and araliphatic ketones;
aromatic and araliphatic carboxylic acids and esters thereof;
nitrogen-containing aromatic compounds;
phenols, phenyl ethers and phenyl esters;
heterocyclic compounds;
lactones and of esters of aliphatic carboxylic acids selected from the group consisting of (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octynoate; methyl-2-nonynoate; allyl-2-isoamyloxyacetate; methyl-3,7-dimethyl-2,6-octadienoate; 4-methyl-2-pentylcrotonate.

7. A perfume composition with a jasmone odour according to claim 6, wherein said perfume oil comprises said mixture of cis- and trans-3-methyl-γ-decalactone in an amount within a range of 0.01 to 99.9 wt. %, based on total weight of the perfume composition.

8. A perfume composition according to claim 6, wherein said mixture of cis-3-methyl-γ-decalactone and trans-3-methyl-γ-decalactone is present in said perfume composition in an amount effective to impart a jasmone odour to said fragrance composition or perfumed article.

9. A process for producing, enhancing or modifying a jasmone odour in a fragrance composition, wherein a quantity of a mixture of cis- and trans-3-methyl-γ-decalactone in a molar ratio in the range of 2:3.5 to 3.5:2 which is sufficient to produce, to enhance or to modify a jasmone odour, is added to the fragrance composition and said fragrance composition comprises a fragrance selected from the group consisting of extracts from natural raw materials including essential oils, concretes, absolutes, resins, resinoids, balsams and tinctures; and individual fragrances from the group of consisting of hydrocarbons;
aliphatic alcohols;
aliphatic aldehydes and acetals thereof;
aliphatic ketones and oximes thereof;
aliphatic sulfur-containing compounds;
aliphatic nitriles;
acyclic terpene alcohols;

acyclic terpene aldehydes and ketones;
cyclic terpene alcohols;
cyclic terpene aldehydes and ketones;
cyclic alcohols;
cycloaliphatic alcohols;
cyclic and cycloaliphatic ethers;
cyclic and macrocyclic ketones;
cycloaliphatic aldehydes;
cycloaliphatic ketones;
esters of cyclic alcohols;
esters of cycloaliphatic alcohols;
esters of cycloaliphatic carboxylic acids;
araliphatic alcohols;
esters of araliphatic alcohols and aliphatic carboxylic acids;
araliphatic ethers;
aromatic and araliphatic aldehydes;
aromatic and araliphatic ketones;
aromatic and araliphatic carboxylic acids and esters thereof;
nitrogen-containing aromatic compounds;
phenols, phenyl ethers and phenyl esters;
heterocyclic compounds;
lactones
and
of esters of aliphatic carboxylic acids selected from the group consisting of (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octynoate; methyl-2-nonynoate; allyl-2-isoamyloxyacetate; methyl-3,7-dimethyl-2,6-octadienoate; 4-methyl-2-pentylcrotonate.

10. A process for the preparation of a fragrance composition with a strong peach odour and a jasmone odour, with the following steps:

preparing a basic fragrance composition which does not have a strong peach odour, wherein said basic fragrance composition comprises a fragrance selected from the group consisting of extracts from natural raw materials including essential oils, concretes, absolutes, resins, resinoids, balsams and tinctures; and individual fragrances from the group of hydrocarbons;
aliphatic alcohols;
aliphatic aldehydes and acetals thereof;
aliphatic ketones and oximes thereof;
aliphatic sulfur-containing compounds;
aliphatic nitriles;
acyclic terpene alcohols;
acyclic terpene aldehydes and ketones;
cyclic terpene alcohols;
cyclic terpene aldehydes and ketones;
cyclic alcohols;
cycloaliphatic alcohols;
cyclic and cycloaliphatic ethers;
cyclic and macrocyclic ketones;
cycloaliphatic aldehydes;
cycloaliphatic ketones;
esters of cyclic alcohols;
esters of cycloaliphatic alcohols;
esters of cycloaliphatic carboxylic acids;
araliphatic alcohols;
esters of araliphatic alcohols and aliphatic carboxylic acids;
araliphatic ethers;
aromatic and araliphatic aldehydes;
aromatic and araliphatic ketones;
aromatic and araliphatic carboxylic acids and esters thereof;
nitrogen-containing aromatic compounds;
phenols, phenyl ethers and phenyl esters;
heterocyclic compounds;
lactones
and
of esters of aliphatic carboxylic acids selected from the group consisting of (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octynoate; methyl-2-nonynoate; allyl-2-isoamyloxyacetate; methyl-3,7-dimethyl-2,6-octadienoate; 4-methyl-2-pentylcrotonate
mixing of the basic fragrance composition with cis-3-methyl-γ-decalactone and trans-3-methyl-γ-decalactone, wherein (i) cis-3-methyl-γ-decalactone and trans-3-methyl-γ-decalactone are used in a molar cis/trans ratio in the range of 2:3.5 to 3.5:2, (ii) the total quantity of cis-3-methyl-γ-decalactone and trans-3-methyl-γ-decalactone used is sufficient to produce the strong peach odour and the jasmone odour and (iii) the quantity of trans-3-methyl-γ-decalactone used is not sufficient in the absence of cis-3-methyl-γ-decalactone to produce the strong peach odour.

11. A fragrance composition or perfumed article with a jasmone odour, comprising a quantity producing the jasmone odour, of a mixture of cis- and trans-3-methyl-γ-decalactone in a molar cis/trans ratio in the range of 2:3.5 to 3.5:2, wherein neither the cis-3-methyl-γ-decalactone used on its own nor the trans-3-methyl-γ-decalactone used on its own produces the jasmone odour, wherein said fragrance composition or said perfumed article comprises a fragrance selected from the group consisting of extracts from natural raw materials such as essential oils, concretes, absolutes, resins, resinoids, balsams and tinctures; and individual fragrances from the group of hydrocarbons;
aliphatic alcohols;
aliphatic aldehydes and acetals thereof;
aliphatic ketones and oximes thereof;
aliphatic sulfur-containing compounds;
aliphatic nitriles;
acyclic terpene alcohols;
acyclic terpene aldehydes and ketones;
cyclic terpene alcohols;
cyclic terpene aldehydes and ketones;
cyclic alcohols;
cycloaliphatic alcohols;
cyclic and cycloaliphatic ethers;
cyclic and macrocyclic ketones;
cycloaliphatic aldehydes;
cycloaliphatic ketones;
esters of cyclic alcohols;
esters of cycloaliphatic alcohols;

esters of cycloaliphatic carboxylic acids;
araliphatic alcohols;
esters of araliphatic alcohols and aliphatic carboxylic acids;
araliphatic ethers;
aromatic and araliphatic aldehydes;
aromatic and araliphatic ketones;
aromatic and araliphatic carboxylic acids and esters thereof;
nitrogen-containing aromatic compounds;
phenols, phenyl ethers and phenyl esters;
heterocyclic compounds;
lactones
and
of esters of aliphatic carboxylic acids selected from the group consisting of (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octynoate; methyl-2-nonynoate; allyl-2-isoamyloxyacetate; methyl-3,7-dimethyl-2,6-octadienoate; 4-methyl-2-pentylcrotonate.

12. A fragrance composition with a jasmone odour according to claim 11, wherein the fragrance composition is a perfume oil composition and the quantity of the mixture of cis- and trans-3-methyl-γ-decalactone used is in the range of 0.01 to 99.9 wt. %, preferably 0.1 to 90 wt. % and particularly preferably 0.5 to 70 wt. %, based on the total weight of the perfume oil composition.

13. A fragrance composition or perfumed article comprising:
a fragrance component wherein said fragrance component is an extract from a raw material and is selected from the group consisting of essential oils, concretes, absolutes, resins, resinoids, balsams and tinctures; and
a mixture of cis- and trans-3-methyl-γ-decalactone in a molar cis/trans ratio of 2:3.5 to 3.5:2, said mixture being present in an amount effective to impart a jasmone odour to said fragrance composition, wherein said cis-3-methyl-γ-decalactone and trans-3-methyl-γ-decalactone alone do not exhibit a jasmone odour.

14. A fragrance composition or perfumed article according to claim 13, wherein said fragrance composition is a perfume oil.

15. A perfumed article comprising:
a perfume oil containing a fragrance and trans-3-methyl-γ-decalactone; and
cis-3-methyl-γ-decalactone in an amount effective to impart a fruity, peach-like note to said perfume oil;
where said fragrance is selected from the group consisting of extracts from natural raw materials such as essential oils, concretes, absolutes, resins, resinoids, balsams and tinctures; and individual fragrances from the group of hydrocarbons;
aliphatic alcohols;
aliphatic aldehydes and acetals thereof;
aliphatic ketones and oximes thereof;
aliphatic sulfur-containing compounds;
aliphatic nitriles;
acyclic terpene alcohols;
acyclic terpene aldehydes and ketones;
cyclic terpene alcohols;
cyclic terpene aldehydes and ketones;
cyclic alcohols;
cycloaliphatic alcohols;
cyclic and cycloaliphatic ethers;
cyclic and macrocyclic ketones;
cycloaliphatic aldehydes;
cycloaliphatic ketones;
esters of cyclic alcohols;
esters of cycloaliphatic alcohols;
esters of cycloaliphatic carboxylic acids;
araliphatic alcohols;
esters of araliphatic alcohols and aliphatic carboxylic acids;
araliphatic ethers;
aromatic and araliphatic aldehydes;
aromatic and araliphatic ketones;
aromatic and araliphatic carboxylic acids and esters thereof;
nitrogen-containing aromatic compounds;
phenols, phenyl ethers and phenyl esters;
heterocyclic compounds;
lactones
and
of esters of aliphatic carboxylic acids selected from the group consisting of (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octynoate; methyl-2-nonynoate; allyl-2-isoamyloxyacetate; methyl-3,7-dimethyl-2,6-octadienoate; 4-methyl-2-pentylcrotonate.

16. A fragrance composition comprising:
a fragrance component; and
a perfume oil including a mixture of cis-3-methyl-γ-decalactone and trans-3-methyl-γ-decalactone in a ratio of 2:3.5 to 3.5:2, said perfume oil being present in an amount effective to impart fruity peach-like notes, coconut-like odour or jasmone odour to said fragrance composition; and
a fragrance selected from the group consisting of extracts from natural raw materials such as essential oils, concretes, absolutes, resins, resinoids, balsams and tinctures; and individual fragrances from the group of hydrocarbons;
aliphatic alcohols;
aliphatic aldehydes and acetals thereof;
aliphatic ketones and oximes thereof;
aliphatic sulfur-containing compounds;
aliphatic nitriles;
acyclic terpene alcohols;
acyclic terpene aldehydes and ketones;
cyclic terpene alcohols;
cyclic terpene aldehydes and ketones;
cyclic alcohols;
cycloaliphatic alcohols;
cyclic and cycloaliphatic ethers;
cyclic and macrocyclic ketones;
cycloaliphatic aldehydes;
cycloaliphatic ketones;
esters of cyclic alcohols;

esters of cycloaliphatic alcohols;
esters of cycloaliphatic carboxylic acids;
araliphatic alcohols;
esters of araliphatic alcohols and aliphatic carboxylic acids;
araliphatic ethers;
aromatic and araliphatic aldehydes;
aromatic and araliphatic ketones;
aromatic and araliphatic carboxylic acids and esters thereof;
nitrogen-containing aromatic compounds;
phenols, phenyl ethers and phenyl esters;
heterocyclic compounds;
lactones
and
of esters of aliphatic carboxylic acids selected from the group consisting of (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octynoate; methyl-2-nonynoate; allyl-2-isoamyloxyacetate; methyl-3,7-dimethyl-2,6-octadienoate; 4-methyl-2-pentylcrotonate.

17. A fragrance composition according to claim 16, wherein said perfume oil comprises 0.01 wt % to 99.9 wt % of said mixture of cis- and trans-3-methyl-γ-decalactone based on the total weight of said perfume oil.

18. A fragrance composition according to claim 16, wherein said perfume oil comprises 0.1 wt % to 90 wt % of said mixture of said cis- and trans-3-methyl-γ-decalactone based on the total weight of said perfume oil.

19. A fragrance composition according to claim 16, wherein said perfume oil comprises 0.5 wt % to 70 wt % of said cis- and trans-3-methyl-γ-decalactone based on the total weight of said perfume oil.

20. A fragrance composition or perfumed article comprising a fragrance component selected from the group consisting of aliphatic alcohols, aliphatic aldehydes and acetals thereof, aliphatic ketones and oximes thereof, aliphatic sulfur-containing compounds, aliphatic nitriles, acyclic terpene alcohols, acyclic terpene aldehydes and ketones, cyclic terpene alcohols, cyclic terpene aldehydes and ketones, cyclic alcohols, cycloaliphatic alcohols, cyclic and cycloaliphatic ethers, cyclic and macrocyclic ketones, cycloaliphatic aldehydes, cycloaliphatic ketones, esters of cyclic alcohols, esters of cycloaliphatic alcohols, esters of cycloaliphatic carboxylic acids, araliphatic alcohols, esters of araliphatic alcohols and aliphatic carboxylic acids, araliphatic ethers, aromatic and araliphatic aldehydes, aromatic and araliphatic ketones, aromatic and araliphatic carboxylic acids and esters thereof, nitrogen-containing aromatic compounds, phenols, phenyl ethers and phenyl esters, heterocyclic compounds, lactones, and of esters of aliphatic carboxylic acids selected from the group consisting of (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octynoate; methyl-2-nonynoate; allyl-2-isoamyloxyacetate; methyl-3,7-dimethyl-2,6-octadienoate; 4-methyl-2-pentylcrotonate; and a mixture of cis- and trans-3-methyl-γ-decalactone in a molar cis/trans ratio of 2:3.5 to 3.5:2, said mixture being present in an amount effective to impart a jasmone odour to said fragrance composition, wherein said cis-3-methyl-γ-decalactone and trans-3-methyl-γ-decalactone alone do not exhibit a jasmone odour.

* * * * *